United States Patent [19]

Harvey et al.

[11] 4,430,998

[45] Feb. 14, 1984

[54] WOUND CLOSING DEVICE

[75] Inventors: Robert J. Harvey, Emeryville; Philip Litwak, Novato, both of Calif.; William A. Ribich, Lexington, Mass.; John M. Dubowik, Nashua, N.H.

[73] Assignee: Thoratec Laboratories Corporation, Berkeley, Calif.

[21] Appl. No.: 383,759

[22] Filed: Jun. 1, 1982

[51] Int. Cl.³ .............................................. A61B 17/08
[52] U.S. Cl. .................................................... 128/335
[58] Field of Search ........................ 128/334, 335, 337

[56] References Cited

U.S. PATENT DOCUMENTS

| 2,421,193 | 5/1947 | Gardner | 128/335 |
| 2,472,009 | 5/1949 | Gardner | 128/337 |
| 3,487,836 | 1/1970 | Niebel et al. | 128/337 X |
| 3,825,010 | 7/1974 | McDonald | 128/335 X |

Primary Examiner—Dalton L. Truluck
Attorney, Agent, or Firm—Lothrop & West

[57] ABSTRACT

A closure band of water-vapor permeable, flexible, elastic plastic spans a cut in the flesh and holds the cut closed. Flesh-engaging penetrants such as hooks are partly embedded in or are part of the band and engage the flesh either side of the cut. Adhesive on the band also contacts the flesh and helps hold the penetrants embedded. A tear strip overlying openings through the band, when removed, allows inspection of the cut.

4 Claims, 8 Drawing Figures

WOUND CLOSING DEVICE

BRIEF SUMMARY OF THE INVENTION

A wound closing device has a flexible, somewhat elastic band with a clear, transparent center and having needles extending from the band on either side of the center to engage the subjacent flesh. Adhesive on one face of the band both sides of the center helps to hold the band against the flesh and the needles embedded. The band is of polyurethane or an elastomer of a character to permit the passage therethrough of water vapor, but not water nor bacteria. In one version there are openings through the center of the band normally closed by an overlying tear strip of suitable wound dressing material with "tear filaments" for its selective removal.

PRIOR ART

Reference is made to U.S. Pat. No. 4,164,943 issued on Aug. 21, 1979 to Hill et al. and assigned to the assignee hereof and listing the following patents:

| 2,046,094 | 6/1936 | Schmidt |
| 2,670,735 | 3/1954 | Brody |
| 3,371,352 | 3/1968 | Siposs et al. |
| 3,630,195 | 12/1971 | Santomieri |
| 3,696,920 | 10/1972 | Lahay |
| 624,676 | 8/1961 | Canadian |

The Hill et al., Siposs et al., Brody and Canadian patents all show means for piercing the flesh, but do so to hold extraneous articles in position. None of these employs an adhesive, and none is concerned with wound closure.

Reference is also made to the following patents:

| 3,601,127 | 8/1960 | Finegold |
| 3,385,299 | 5/1968 | Le Roy |
| 3,825,010 | 7/1974 | McDonald |

While these patents are concerned with wound closure, the Finegold disclosure includes several separate, relatively rigid parts telescoping with each other into various positions held by ridges or serrations. The Le Roy patent also has several, separate relatively rigid parts telescoping with each other into various positions held by a ratcheting device. The McDonald patent has an applicator strap of three contiguous sections, the relatively stiff end sections overlying subjacent carrier strips, each of which has needles projecting therefrom into the skin on either side of a wound. None of these patents is concerned with dual attachment of a closure device to the skin by needles and by adhesive.

DETAILED DESCRIPTION

Figure 1:
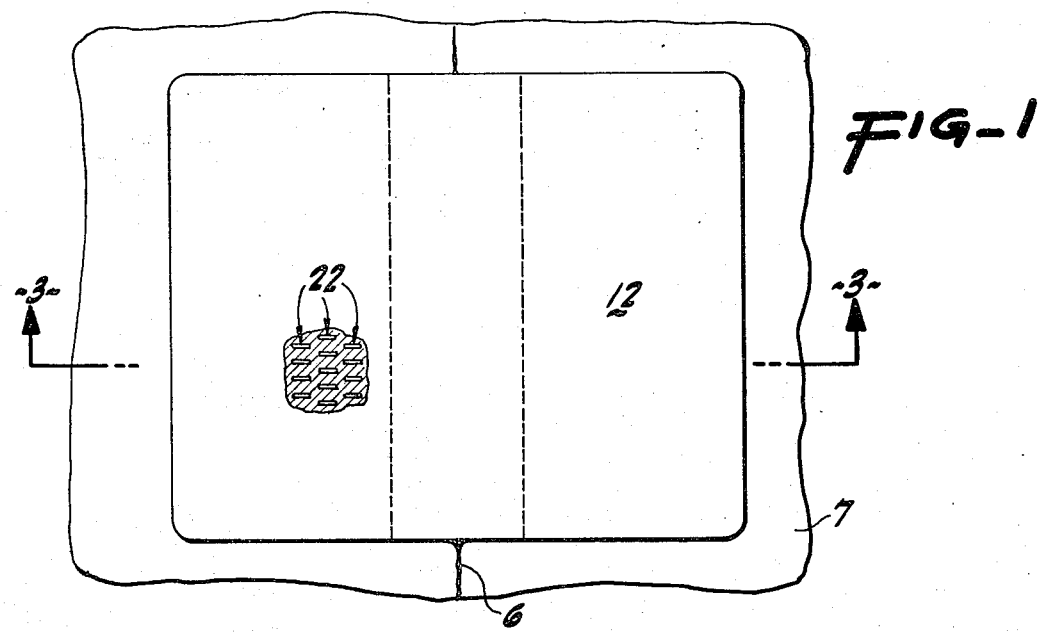
FIG. 1 is a plan, with various portions broken away to reduce the size of the figure and to reveal interior construction, of a wound closing device pursuant to the invention.

It is customary to close operative and similar approximately linear wounds in the body primarily by bringing the edges of the wound together at the cut and then suturing to hold the juxtaposed, cut surfaces together. While this is satisfactory in a large number of instances, in other instances, particularly for some internal operations, it requires a great deal of time, does not necessarily produce a smoothly continuous ultimate juncture, and requires substantial effort not only to place the sutures in the first instance, but likewise to remove them ultimately.

To avoid these and other attendant difficulties and to provide a substantially improved device for wound closure, we provide an arrangement particularly useful in connection with an approximately straight or rectilinear cut or wound 6 through the epidermis 7 and into the dermis 8. Left unattended, the wound 6 tends to permit the two sides 9 and 11 to separate from each other to leave an intervening, often misaligned, gap which eventually will close with substantial scar tissue. This result is avoided by the provision of a band 12 comprised of a generally flexible, somewhat elastic material such as polyurethane or an equivalent plastic. A band of this nature, about 1 to 15 mils thick, is preferably transparent and is preferably capable of permitting the passage of water vapor, but precludes the passage therethrough of water itself and of bacteria. The band is of nearly uniform thickness and usually about 3 to 5 centimeters wide in the direction of the wound length, or less, although it may vary somewhat, and extends between an outer face 16 and an inner face 17 on the side of the skin 8.

Figure 2:
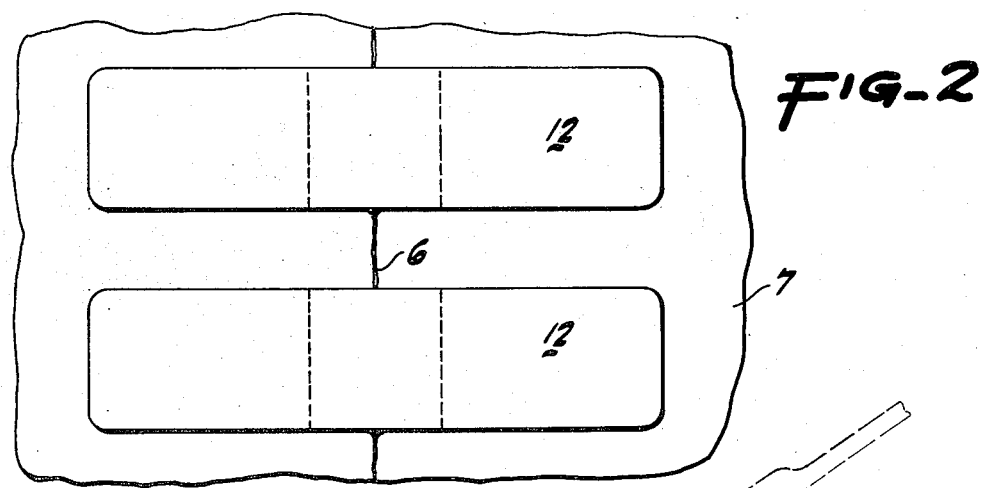
FIG. 2 is a plan similar to FIG. 1, but of a modified form of the wound closing device.
Figure 7:
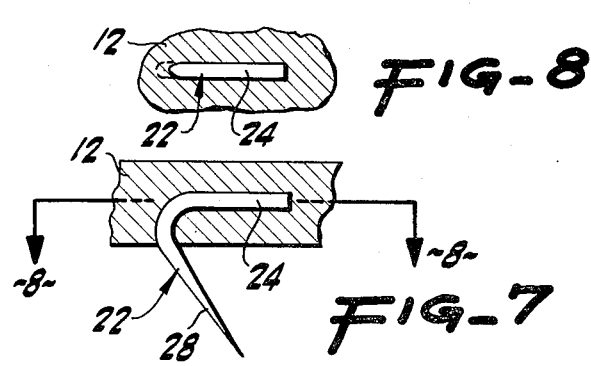
FIG. 7 is a detail showing a hook in enlarged form.

Customarily, the band is of generally rectangular aspect and can be relatively wide in a direction across the wound length or long in a direction along the wound length as shown in FIG. 1 or it can be as long as 50 to 70 centimeters for use in closing long surgical incisions. Alternatively, it can be of similar or smaller width but much shorter for use in multiple as shown in FIG. 2. The band has a central section 18 designed to overlie the wound or cut 6 and has continuous side portions 19 and 21 that are generally similar to each other and are symmetrical about the center portion of the device. Each of the side portions is provided with at least one skin penetrating device such as one hook 22 or one row of hooks 22 of a particular configuration. Each penetrant may be a separate member and curved or relatively straight, as shown in FIG. 7. Preferably, a large number of relatively small, separate hooks 22 is partially embedded in each of the side portions 19 and 21 to distribute the stresses and so apply a substantially uniform force on the adjacent skin to hold the wound closed. The use of several penetrants reduces the load on each one and on the adjacent skin. The hooks can be arranged in geometrically regular rows and ranks, or in spaced clusters or may be provided in a staggered or even random array about 0.08 inches apart, as shown in FIG. 1. The preference is that the effects of the individual penetrants can be appropriately distributed among them and over the skin.

Each of the hooks 22 is inclusive of a base 24 and is preferably comprised of a physiologically inert material such as some of the more rigid plastics, or of titanium or of stainless steel. Each of the hook bases 24 is relatively straight and can be disposed between and preferably centrally between the upper and lower faces 16 and 17 of the band. The hooks 22 can, if desired, be accommodated in a thickened part of the side portions 19 and 21 defining shoulders a and b or ridges extending across the band in the direction of the wound length. The base of the hook is of sufficient extent so that it stays readily in place in its surrounding band and does not tend to rotate or shift and loosen in any particular direction even under the maximum forces normally imposed. The base 24 may be joined to and act in common with the base 24 of an adjacent hook but without substantially reducing the flexibility or elasticity of the band transversely; i.e. in the direction of the length of the wound.

The hook continues from the base 24 into a needle 28 merging smoothly with the base and extending to emerge from or through the face 17. Alternatively, by use of a suitable, single plastic, the distinct hook base 24 can be eliminated and in effect merged with or form part of the band 12. The penetrant or needle 28 then also merges with the band, being of the same material and integral therewith. The needle, of whatever material and curved or straight, is about 0.25 to 1.5 millimeters long, tapers to a point and is generally directed or inclined toward the central portion of the structure. The needles 28 on opposite sides of the center converge toward each other in directions as indicated.

With a band of the sort so far described, the device can be attached to the sublying flesh by first inserting the needles on one side of center into the flesh and, by an approximate rotation, then stretching the band slightly and inserting the needles of the other side of center into the then abutted flesh. Preferably, the penetrants or needles are of a length so that they penetrate the epidermis 7 but are not long enough to penetrate into the dermis 8, although, if desired, it is easy to make the needles long enough to penetrate both the epidermis and the dermis. With a device as described, and as positioned, the sides 9 and 11 defined by the cut 6 are at least partially drawn together and are held in good, registering or aligned abutment. The amount of resiliency in the band maintains some tension on the two sides so that they tend to remain in contact despite external stresses. There are sufficient needles employed so that the desired compression or contact force is distributed and imposed upon the portions that ultimately grow together.

In addition to the elementary form just described, there is a version in which the skin side or inner face 17 of the band 12 is provided with a limited layer 33 of an appropriate adhesive effective not only on the plastic material of the band but, also effective on the underlying epidermis. There is another limited layer 34 of adhesive in symmetry with the layer 33. Actually, in practice the adhesive layer is quite thin, but for purposes of illustration herein it is shown as having substantial thickness, as are some other parts of the structure.

The adhesive preferably covers virtually all of the face 17 of the band except possibly in a central zone or area in the vicinity of the cut 6. Adhesive may be omitted in that area. The primary purpose of the adhesive is to hold the strip 19 against the epidermis of the skin, thereby aiding in keeping the needles well and properly embedded in the skin. A secondary function is to cooperate with the needles to hold the two sides in position.

Figure 3:
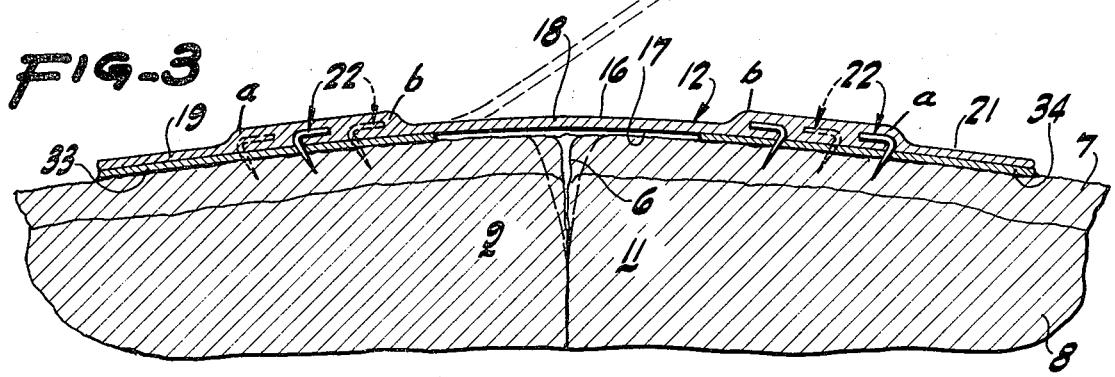
FIG. 3 is a cross-section, the plane of which is indicated by the line 3—3 of FIG. 1.
Figure 4:
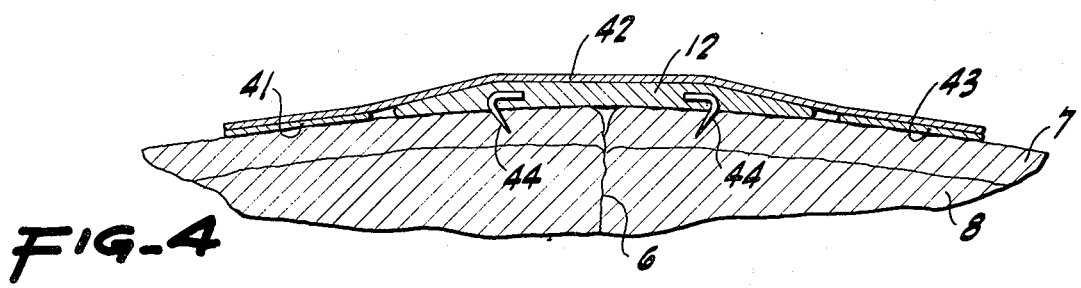
FIG. 4 is a cross-section, similar to FIG. 3, but showing a modified form of device.

In a variation, as shown in FIG. 4, there are areas 41 and 43 of adhesive just along the outer edges of the cover 42. It is not necessary in many cases to have the adhesive extend into or onto the area occupied by the various hooks 44. The adhesive in the outer edges is effective in holding the side portions of the strip 19 firmly against the skin, thus preventing the hooks from retracting from the skin. While but one hook on each side is shown in this figure, it is understood that any desired number may be employed as shown in FIGS. 1 and 3, for example.

Figure 5:
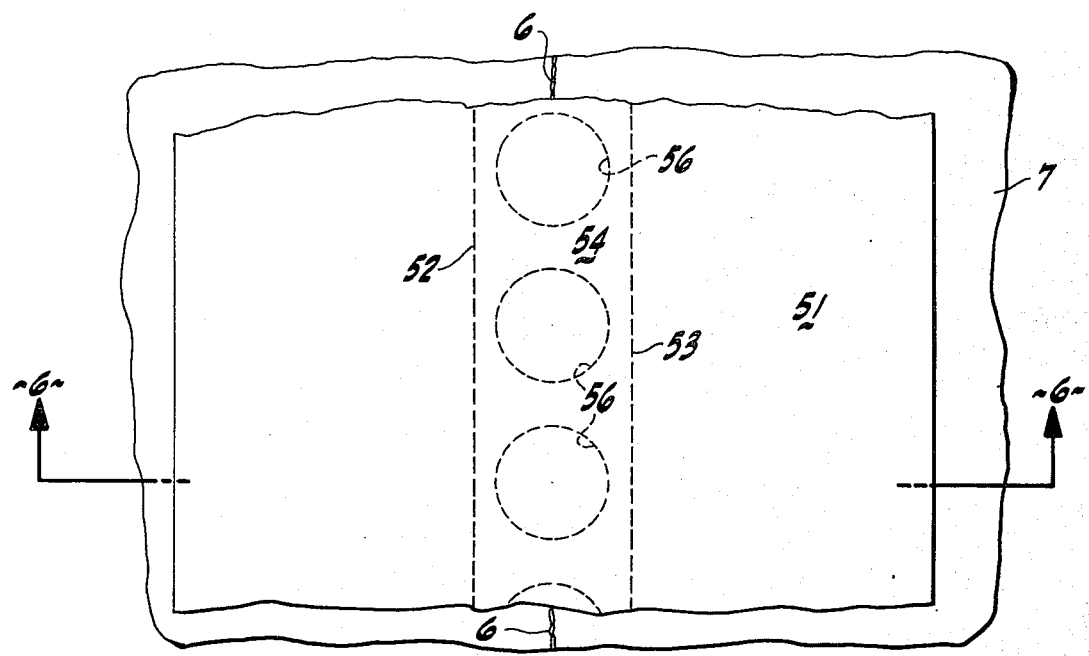
FIG. 5 is a plan, with portions broken away to reduce the size of the figure, showing a further modified form of device.
Figure 6:
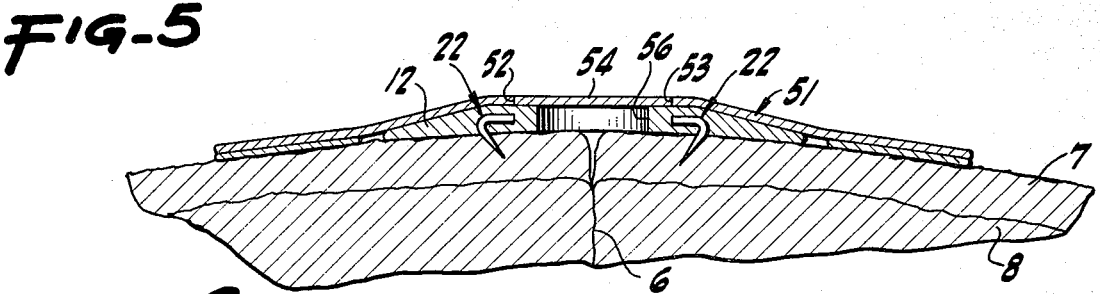
FIG. 6 is a cross-section, the plane of which is indicated by the line 6—6 of FIG. 5.
Figure 8:
FIG. 8 is a cross-section, the plane of which is indicated by the line 8—8 of FIG. 7.

In another version of the arrangement, as indicated in FIGS. 5 and 6, the construction is approximately that of FIG. 4 except that the overlying layer, designated 51, is provided along its central portion with weakened longitudinal sections 52 and 53, either side of center. This leaves an intervening tear strip 54 normally overlying a plurality of inspection openings 56 through the band 12. With this arrangement, while the attachment and use of the band are as before, it is possible for the attending physician, anytime after the holding device has been secured, to tear out the section 54 to inspect the adjacent parts. He is then able to inspect the adjacent portions of the cut through the openings 56. If the openings are of sufficient size, he can also palpate the subjacent material to judge its condition. After an inspection, the tear strip 54 can be replaced by an overlying sealing strip, not shown, or the wound can be left open to air if deemed advisable.

With any of the arrangements as disclosed herein, it is possible entirely to avoid the use of sutures, and to provide a band, conveniently in a roll form, for continuous application over and along the direction of an extended incision so as to hold together the separate flesh portions alongside the incision.

When the wound has sufficiently healed, then it is easy to reverse the application technique and lift out one side of the band from the flesh by first lifting either one of the side portions 19, starting at its outermost edge and rotating upward and centrally toward the wound. This causes the hooks to retract with ease and without unnecessary trauma to the adjacent tissue. The process is then repeated on the other side portion of the band by similarly dislodging the hooks.

Through the use of this device it is possible entirely to eliminate the use of sutures or staples in the vast majority of the cases requiring skin closure and the necessity or the rather arduous and somewhat painful positioning and removal of them. It is also possible to provide a more nearly continuous and effective holding of the sides of the cut together so that healing in proper registry is effectuated uniformly with minimum wound trauma and scarring trauma.

We claim:

1. A wound closing device for engaging the flesh adjacent an elongated cut comprising a band of flexible material of predetermined thickness having an inside face and an outside face, a pair of integral rib portions each upstanding from said outside face and spaced from each other to leave a central portion of said band of said predetermined thickness adapted to overlie said cut and spaced from the ends of said band to leave side portions of said band of said predetermined thickness, means defining areas of adhesion on said inside face at said side portions thereof, and a pair of individual hooks, each hook having a base embedded in a respective one of said rib portions and having a needle connected to said base and extending therefrom and projecting through said inside face adjacent an area of adhesion, said needles being in positions converging toward each other.

2. A device as in claim 1 in which each of said rib portions includes a plurality of said hooks, all of said hooks in one of said rib portions having said needles thereof substantially parallel to each other.

3. A device as in claim 1 in which said needle is curved.

4. A device as in claim 1 in which said band is elastic.

* * * * *